US00PP36544P3

(12) United States Plant Patent
Block

(10) Patent No.: US PP36,544 P3
(45) Date of Patent: Mar. 11, 2025

(54) ***ANTHURIUM* PLANT NAMED 'BLOCANTMIC'**

(50) Latin Name: *Anthurium magnificum*
Varietal Denomination: BLOCANTMIC

(71) Applicant: Jeffrey Sherwood Block, Miami, FL (US)

(72) Inventor: Jeffrey Sherwood Block, Miami, FL (US)

( * ) Notice: Subject to any disclaimer, the term of this patent is extended or adjusted under 35 U.S.C. 154(b) by 0 days.

(21) Appl. No.: 18/831,045

(22) Filed: May 15, 2024

(65) Prior Publication Data

US 2024/0389489 P1 Nov. 21, 2024

(30) Foreign Application Priority Data

May 16, 2023 (QZ) ..... PBR 2023/1067

(51) Int. Cl.
*A01H 5/02* (2018.01)
*A01H 6/10* (2018.01)

(52) U.S. Cl.
USPC ..... Plt./365
CPC ..... *A01H 6/10* (2018.05)

(58) Field of Classification Search
USPC ..... Plt./365
CPC ..... A01H 5/02
See application file for complete search history.

*Primary Examiner* — Kent L Bell
(74) *Attorney, Agent, or Firm* — Samuel R. McCoy, Jr.

(57) ABSTRACT

'BLOCANTMIC' is a new and distinctive variety of *Anthurium* plant which is characterized by the combination of vigorous growth, dark greyed-purple petioles, mature foliage with a dark green general coloration of the upper foliar surface with light greyed-green veins, a very light greyed-green lower leaf surface with greyed-red foliar venation, and the stability of all characteristics from generation to generation.

3 Drawing Sheets

Latin name of the genus and species: The Latin name of the genus and species of the novel variety disclosed herein is *Anthurium magnificum.*

Variety denomination: The inventive variety of *Anthurium* disclosed herein has been given the variety denomination 'BLOCANTMIC'.

BACKGROUND OF THE INVENTION

Parentage: The new cultivar is a seedling selection which resulted from the multigenerational, controlled self-pollination of an unnamed *Anthurium magnificum* plant (not patented) carried out in Miami, Floria. Over a period of thirty years, the inventor self-crossed the parent plant through four distinct generations. With each progeny population of approximately 250 to 500 seedling accessions, the inventor evaluated for a superior combination of improved plant vigor and unique foliage with the darkest upper leaf surface and lightest lower leaf surface with conspicuous dark red veins. In May of 2019, one progeny from the fourth generation of accessions was observed to exhibit the best combination of these characteristics. After further evaluation to confirm the unique characteristics, the new cultivar was selected in April of 2022 for commercialization and given the breeder denomination 'BLOCANTMIC'.

Asexual Reproduction: Asexual reproduction of 'BLOCANTMIC', by way of meristematic tissue culture, was first performed in April of 2022 in Eustis, Florida. Multiple successive generations so produced have shown that the unique features of the instant cultivar are stable and reproduced true to type.

SUMMARY OF THE INVENTION

The cultivar 'BLOCANTMIC' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Anthurium* cultivar 'BLOCANTMIC'. These traits, in combination, distinguish 'BLOCANTMIC' as a new and distinct cultivar.

1. *Anthurium* 'BLOCANTMIC' is a vigorously-growing herbaceous perennial with a flattened spherical profile; and
2. *Anthurium* 'BLOCANTMIC' exhibits durable foliage borne on dark greyed-purple petioles; and
3. *Anthurium* 'BLOCANTMIC' exhibits juvenile foliage with an adaxial surface that is colored with a mixture of dark greyed-green and brown and veins that are colored greyed-red; and
4. *Anthurium* 'BLOCANTMIC' exhibits juvenile foliage with an abaxial surface that is colored a very light greyed-green and veins that are colored greyed-purple; and
5. *Anthurium* 'BLOCANTMIC' exhibits mature foliage with an adaxial surface that is colored with a mixture of dark greyed-green and yellow-green and veins that are colored with a light shade of greyed-green; and
6. *Anthurium* 'BLOCANTMIC' exhibits mature foliage with an abaxial surface that is colored a very light greyed-green and veins that are colored greyed-red.

Figure 1:
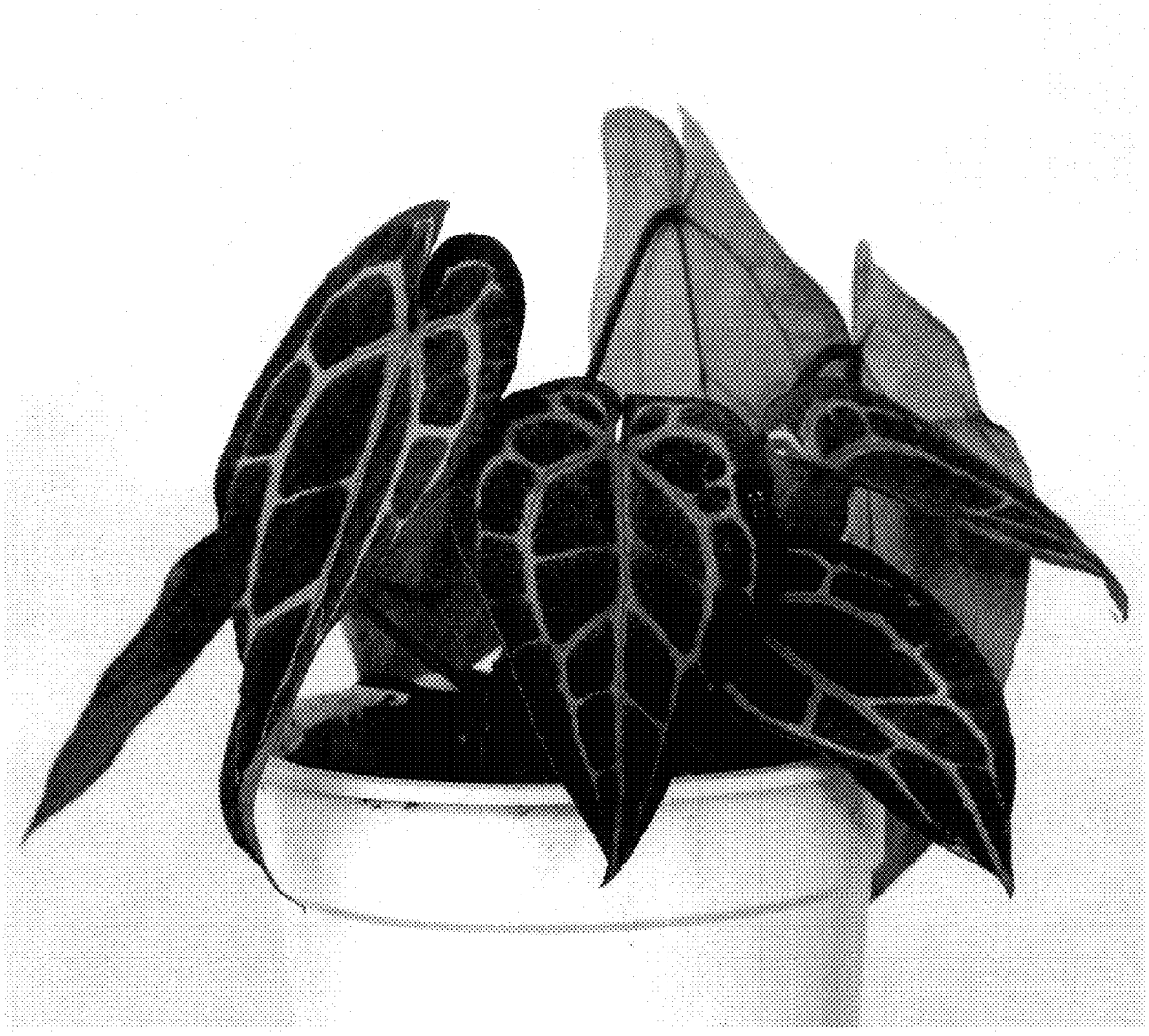
FIG. 1 shows, as nearly true as it is reasonably possible to make the same in color illustrations of this type, an exemplary mature plant of 'BLOCANTMIC', grown in a greenhouse in Honselerdijk, the Netherlands. The plant shown is 14 months old, potted into a 21 cm nursery pot.
Figure 2:
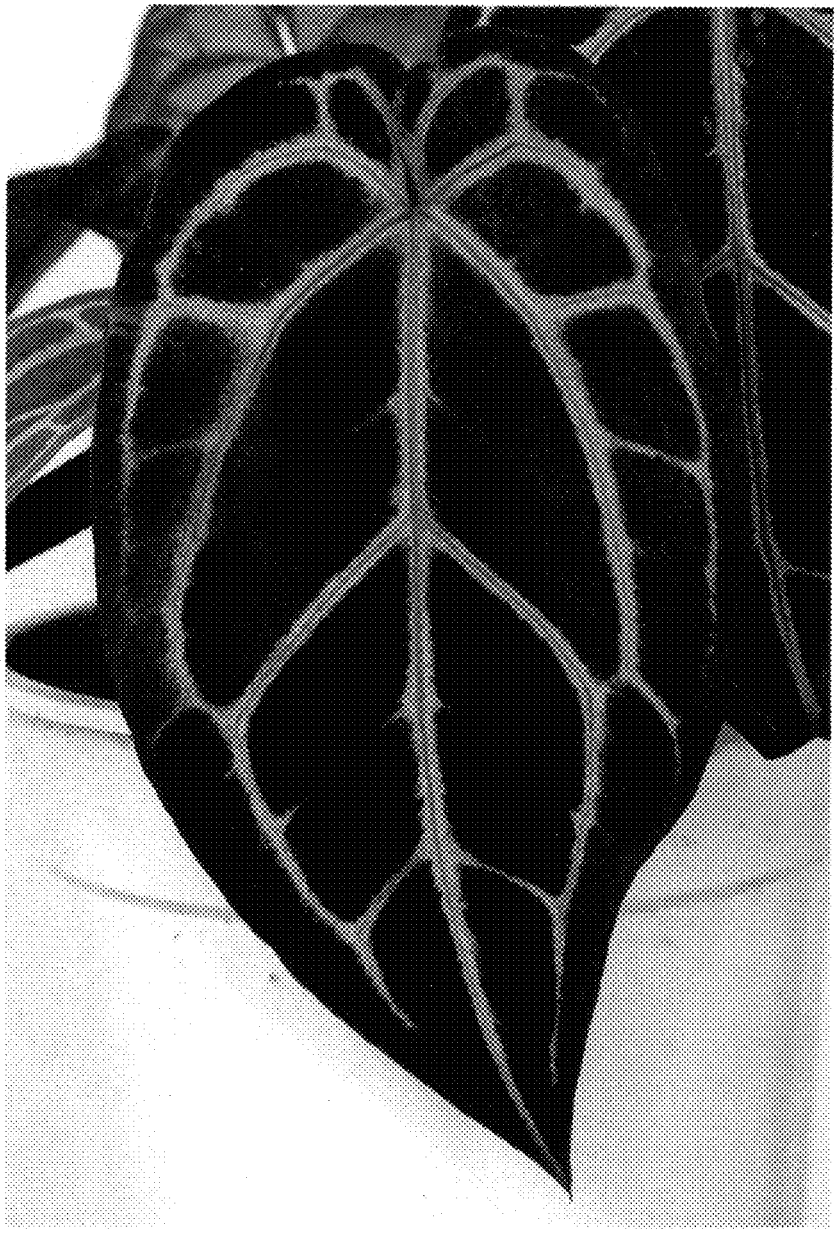
FIG. 2 shows, as nearly true as it is reasonably possible to make the same in color illustrations of this type, the typical juvenile foliage of 'BLOCANTMIC'.
Figure 3:
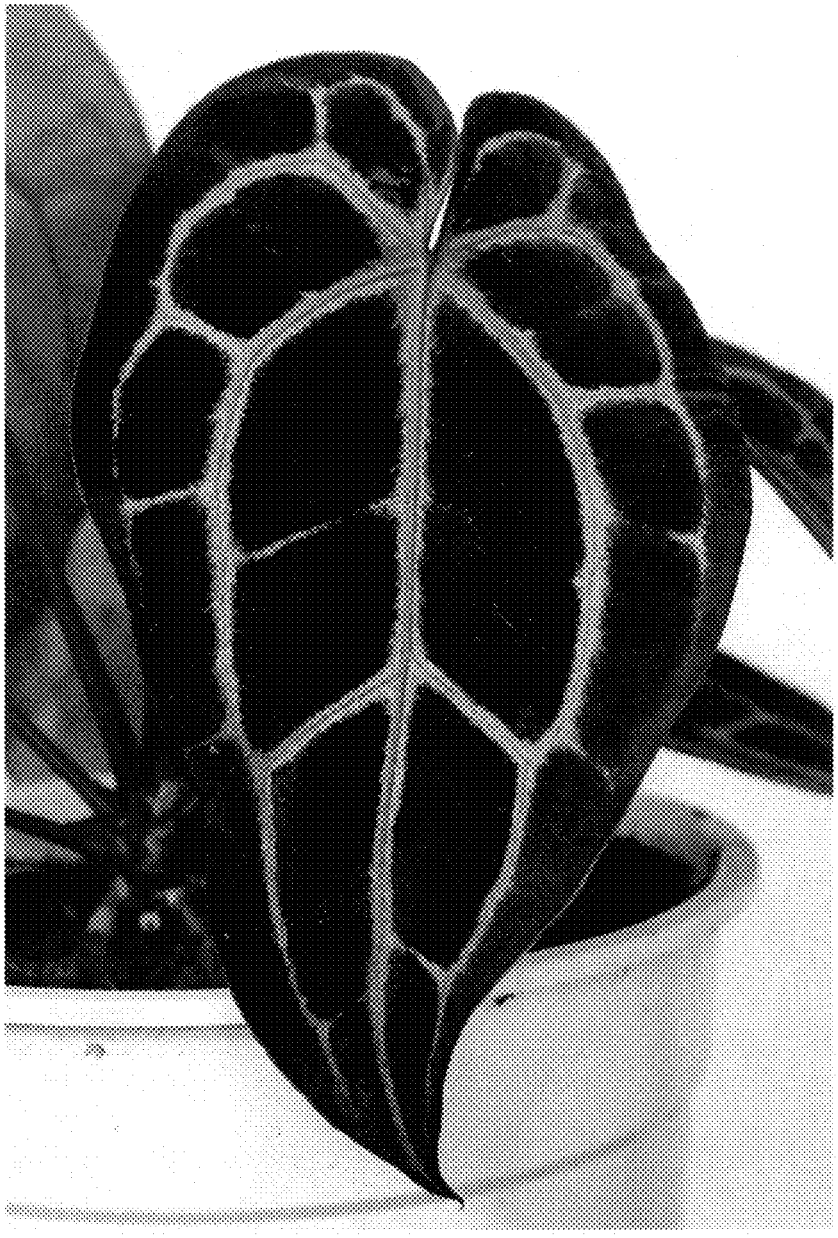
FIG. 3 shows, as nearly true as it is reasonably possible to make the same in color illustrations of this type, the typical mature foliage of 'BLOCANTMIC'.

The photographs were taken using conventional techniques and although colors may appear different from actual colors due to light reflectance it is as accurate as possible by conventional photographic techniques.

BOTANICAL DESCRIPTION OF THE PLANT

The following is a detailed botanical description of a new and distinct variety of *Anthurium* known as 'BLOCANTMIC', based upon observations made from 14-month-old plants grown in 21 cm nursery containers. Plants were grown in a greenhouse in Honselerdijk, The Netherlands and were produced using conventional greenhouse production protocols for *Anthurium*. Observation data was recorded in April of 2024.

Those skilled in the art will appreciate that certain characteristics will vary with older or, conversely, with younger plants. 'BLOCANTMIC' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, sixth edition.

A botanical description of 'BLOCANTMIC' and a comparison with the parent and most similar variety are provided below.

General plant description:

*Growth rate*.—Fast-growing.

*Plant vigor*.—Vigorous.

*Growth habit*.—Clump-forming, herbaceous perennial.

*Plant profile shape*.—Flattened spherical.

*Height*.—20.9 cm in height, to the highest leaf.

*Width*.—Average 34.5 cm in width.

*Propagation*.—Meristematic tissue culture.

*Time to initiate roots*.—Approximately 25 to 30 days to initiate roots at approximately 25 degrees Celsius.

*Time to produce a marketable plant*.—Approximately 28 weeks to produce a marketable plant in a 14-cm container at an approximate average ambient temperature range of 22 to 32 degrees Celsius.

*Environmental tolerances*.—Adapt to, at least, USDA Zones 10 to 13 and temperatures ranging from as high as 40 degrees Celsius and as low as 5 degrees Celsius; moderate to high tolerance to rain; low tolerance to wind.

*Pest and pathogen resistance and susceptibility*.—Plants have not been observed to be susceptible or resistant to pathogens and pests common to *Anthurium*.

Root system:

*General*.—A moderately shallow root system with fleshy adventitious roots arising from the plant crown.

*Branching*.—Freely branched.

*Density*.—Moderately dense.

*Distribution*.—Relatively shallow.

*Texture*.—Fleshy; smooth; lacking root hairs.

*Color*.—Nearest to a combination of white and greyed-yellow, nearest to RHS NN155D and 162C.

Stems:

*General*.—Acaulescent with foliage that arises directly from the base of the plant, at the soil level, forming basal clumps; no stems or lateral branches are produced.

*Quantity of clumps per plant*.—2.

Foliage:

*Arrangement*.—Alternate.

*Division*.—Simple.

*Quantity of leaves per lateral branch*.—3 leaves per clump.

*Leaf shape*.—Cordate to narrow cordate.

*Leaf apex*.—Apiculate.

*Leaf base*.—Cordate; lobes overlapping.

*Aspect*.—Moderately to strongly concave.

*Leaf length*.—Average 19.4 cm in length.

*Leaf width*.—Average 11.9 cm in width.

*Leaf margin*.—Entire; slightly undulate.

*Texture, adaxial surface*.—Moderately to strongly bullate, glabrous, and coriaceous.

*Texture, abaxial surface*.—Moderately to strongly bullate, glabrous, and coriaceous.

*Luster, adaxial surface*.—Matte to slightly glossy.

*Luster, abaxial surface*.—Matte.

*Juvenile color, adaxial surface*.—Nearest to a mixture of greyed-green and brown, RHS N189A and 200A yet darker, and veined greyed-red, nearest to RHS 181A; areas of the lamina that are adjacent to the veins are colored grey, nearest to RHS 201D, with a conspicuous silvery sheen.

*Juvenile color, abaxial surface*.—Greyed-green, nearest to RHS 197C, and veined greyed-purple, nearest to RHS 185A.

*Mature color, adaxial surface*.—Nearest to a mixture of yellow-green and greyed-green, RHS 147A and N189A yet darker; areas of the lamina that are adjacent to the veins are colored black, nearest to RHS 202D, with a conspicuous silvery sheen.

*Mature color, abaxial surface*.—Greyed-green, nearest to RHS 194A yet slightly darker.

*Venation*.—Vein pattern — Pinnate. Mature vein color, adaxial surface — Greyed-green, RHS 197B. Mature vein color, abaxial surface — Greyed-red, nearest to in between RHS 181A and 181B.

*Petiole*.—Aspect — Terete. Length — 13.4 cm, including the geniculum. Width — 0.4 cm. Texture and luster, both surfaces — Smooth, glabrous and slightly glossy. Color, adaxial surface — Greyed-purple, nearest to RHS 183A, and suffused with brown, nearest to RHS 200B. Color, abaxial surface — Greyed-purple, nearest to RHS 183A, and suffused with brown, nearest to RHS 200B. Strength — Strong. Geniculum — Length — 1.4 cm. Height — 0.35 cm. Width — 0.3 cm. Color, adaxial surface — Greyed-purple, nearest to RHS 187A. Color, abaxial surface — Greyed-purple, nearest to RHS 187B. Petiole wings — Length — Approximately 3.3 cm. Width — Approximately 0.6 cm. Color — Greyed-red, nearest to a mixture of RHS 178B and 178C.

Inflorescence:

*Type*.—Consisting of a spathe and spadix, with the spathe subtending the spadix prior to anthesis and becoming progressively more reflexed as the inflorescence ages.

*Arrangement*.—Placed atop the peduncle.

*Position*.—Inflorescences are carried above the leaf plane.

*Quantity per plant*.—2.

*Natural flowering season*.—Late winter into summer.

*Length*.—15.25 cm.

*Time to flowering*.—13 weeks.

*Fragrance*.—Non fragrant.

*Self-cleaning or persistent*.—Persistent.

*Flower longevity*.—Flowers stay in good condition for approximately 4 weeks.

*Peduncle*.—Cross-section — Elliptical. Attitude — Approximately 15 degrees to the lateral branch axis. Length — Approximately 25.2 cm. Diameter — Approximately 0.4 cm. Texture and luster, both surfaces — Smooth, glabrous, and glossy. Color — Greyed-purple, a blend of RHS 184A, 184B, and 185B. Strength — Strong.

Spathe:

*Attitude*.—At anthesis, averaging 10 degrees to horizontal; apex pointed downward at an average angle of 120 degrees to the spathe.

*Length*.—Approximately 7.9 cm.

*Width*.—Approximately 4.0 cm.

*Shape*.—Lanceolate; basal lobes free to touching.

*Aspect*.—Deeply concave and curled inward towards the peduncle.

*Margin*.—Entire; lightly undulated.

*Apex*.—Narrowly acute.

*Base*.—Obtuse; sessile attachment.

*Texture and luster, upper surface*.—Moderately rugose, glabrous, and matte.

*Texture and luster, lower surface*.—Moderately rugose, glabrous, and matte.

*Color*.—Upper surface, when opening — Greyed-purple, nearest to a blend of RHS 186B and 186C. Lower surface, when opening — Greyed-orange to greyed-red, nearest to RHS 176C and 180C. Upper surface, when fully opened — Greyed-red to greyed-purple, nearest to a combination of RHS 178A and 183B, and slightly darker towards the margins, nearest to RHS 187A. Spathe color does not fade. Lower surface, when fully opened — Greyed-red to greyed-purple, nearest to a combination of RHS 178A and 183B, and slightly darker towards the margins, nearest to RHS 187A. Spathe color does not fade. Venation on the upper surface, when fully opened — Greyed-red, nearest to RHS 179A and 181A and slightly darker towards the apex, nearest to RHS 178A. Venation on the lower surface, when fully opened — Greyed-red, nearest to RHS 178A.

Spadix:

*Attitude*.—Approximately 110 degrees to the spathe.

*Aspect*.—Straight to weakly incurved.

*Shape*.—Cylindrical.

*Apex*.—Obtuse.

*Base*.—Obtuse.

*Length*.—Approximately 12.0 cm.

*Width*.—Approximately 0.9 cm.

*Texture and luster*.—Smooth, glabrous, and very glossy.

*Color*.—When opening — Greyed-purple, nearest to a blend of RHS 186B and 186C. When fully opened — Color — Greyed-purple, a blend of RHS 184A, 184B, and 185B.

*Quantity of flowers per spadix*.—Approximately 150.

*Spadix flower arrangement*.—Rotate.

*Spadix flower shape*.—Flattened; rotate.

*Spadix flower diameter*.—Approximately 2.5 mm.

*Spadix flower depth*.—Approximately 0.75 mm.

Reproductive organs:

*Androecium*.—Stamen quantity — 4. Filament — Length — Approximately 0.1 mm long. Color — Light yellow-orange; RHS color designations cannot be determined due to the minute nature of the filament. Anther — Anther shape — Oblong with a longitudinal slit forming two halves. Anther size — 0.5 mm long and 0.25 mm in diameter. Anther color — White, nearest to RHS 155B. Pollen — None observed.

*Gynoecium*.—Pistil quantity — One. Length — 0.5 mm. Stigma — Shape — Club-shaped. Dimensions — Approximately 0.25 mm across and 0.15 mm tall. Color — Greyed-yellow, nearest to RHS 160D but lighter. Style — Length — 0.25 mm. Color — Very light yellow-green; RHS color designations cannot be determined due to the minute nature of the filament. Ovary — Color — Yellow-green, nearest to RHS 144B.

Seed and fruit: Seed production has not been observed.

Comparisons With the Parent

Plants of the new cultivar 'BLOCANTMIC' differ from the parent, an unnamed *Anthurium magnificum* plant (not patented), in the following characteristics described in Table 1 below.

TABLE 1

| Characteristic | 'BLOCANTMIC' | The parent. |
|---|---|---|
| Plant height. | Shorter than the parent. | Taller than 'BLOCANTMIC'. |
| Foliage shape; length-to-width ratio of the lamina. | Cordate to narrow cordate; length-to-width ratio of 1.6. | Cordate to broadly cordate; length-to-width ratio of 1.3. |
| Size of the mature foliage. | Smaller than the parent. | Larger than 'BLOCANTMIC'. |
| Foliage texture. | Moderately to strongly bullate. | Smooth to slightly bullate. |
| General coloration of the petiole. | A mixture of greyed-purple and brown. | A mixture of yellow-green and greyed-green. |

Comparisons With the Most Similar Variety of Common Knowledge

Plants of the new cultivar 'BLOCANTMIC' differ from the commercial variety, *Anthurium magnificum* x *crystallinum* 'Zara' (not patented), in the following characteristics described in Table 2 below.

TABLE 2

| Characteristic | 'BLOCANTMIC' | 'Zara' |
|---|---|---|
| Foliage shape. | Cordate to narrowly cordate. | Cordate to broadly cordate. |
| Foliage texture. | Moderately to strongly bullate. | Strongly bullate. |
| General coloration of the mature adaxial foliar surface. | A mixture of yellow-green and greyed-green, generally appearing as a very dark green. | A mixture of yellow-green and greyed-green, generally appearing as a lighter shade of green. relative to 'BLOCANTMIC'. |
| General coloration of the mature | Greyed-green. | Vivid red-purple. |

TABLE 2-continued

| Characteristic | 'BLOCANTMIC' | 'Zara' |
|---|---|---|
| foliar veins on the adaxial surface. | | |
| General coloration of the mature abaxial foliar surface. | A lighter shade of greyed-green, relative to 'Zara'. | A darker shade of greyed-green, relative to 'BLOCANTMIC'. |

That which is claimed is:

1. A new and distinct variety of *Anthurium* plant named 'BLOCANTMIC', substantially as described and illustrated herein.

* * * * *